(12) United States Patent
Sueda et al.

(10) Patent No.: US 9,404,195 B2
(45) Date of Patent: Aug. 2, 2016

(54) HEXAGONAL PRISM-SHAPED ZINC OXIDE PARTICLES, METHOD FOR PRODUCTION OF THE SAME, AND COSMETIC, HEAT RELEASING FILLER, HEAT RELEASING RESIN COMPOSITION, HEAT RELEASING GREASE, AND HEAT RELEASING COATING COMPOSITION COMPRISING THE SAME

(75) Inventors: Satoru Sueda, Fukushima (JP); Mitsuo Hashimoto, Fukushima (JP); Atsuki Terabe, Fukushima (JP); Nobuo Watanabe, Fukushima (JP); Koichiro Magara, Fukushima (JP)

(73) Assignee: Sakai Chemical Industry Co., Ltd., Osaka (JP)

( * ) Notice: Subject to any disclaimer, the term of this patent is extended or adjusted under 35 U.S.C. 154(b) by 214 days.

(21) Appl. No.: 14/113,108

(22) PCT Filed: Apr. 26, 2012

(86) PCT No.: PCT/JP2012/061281
§ 371 (c)(1),
(2), (4) Date: Nov. 4, 2013

(87) PCT Pub. No.: WO2012/147887
PCT Pub. Date: Jan. 11, 2012

(65) Prior Publication Data
US 2014/0058029 A1    Feb. 27, 2014

(30) Foreign Application Priority Data
Apr. 28, 2011  (JP) .................................. 2011-101022

(51) Int. Cl.
*C30B 7/14*    (2006.01)
*C08K 3/22*    (2006.01)
(Continued)

(52) U.S. Cl.
CPC .................. *C30B 7/14* (2013.01); *A61K 8/0245* (2013.01); *A61K 8/27* (2013.01); *A61Q 1/02* (2013.01);
(Continued)

(58) Field of Classification Search
CPC ........ C30B 7/14; C30B 29/16; A61K 8/0245; A61K 8/0241; A61K 8/27; C09G 9/02; C01P 2004/40; C01P 2004/54; C01P 2004/62; C01P 2004/11
USPC .............................. 524/432; 428/402; 117/68
See application file for complete search history.

(56) References Cited

U.S. PATENT DOCUMENTS

| 2011/0081548 A1 | 4/2011 | Sueda et al. | |
| 2011/0081550 A1* | 4/2011 | Sueda | C01G 9/02 428/402 |
| 2012/0097888 A1* | 4/2012 | Takabatake | B82Y 30/00 252/75 |

FOREIGN PATENT DOCUMENTS

| JP | H03-183620 A | 8/1991 |
| JP | H11-302015 A | 11/1999 |

(Continued)

OTHER PUBLICATIONS

Garcia, S.P., et al., "Controlling the Morphology of Zinc Oxide Nanorods Crystallized from Aqueous Solutions: The Effect of Crystal Growth Modifiers on Aspect Ratio", *Chemistry of Materials*, 2007, 19, pp. 4016-4022.

(Continued)

*Primary Examiner* — Ling Choi
*Assistant Examiner* — Catherine S Branch
(74) *Attorney, Agent, or Firm* — Polsinelli PC

(57) ABSTRACT

It is an object of the present invention to provide hexagonal prism-shaped zinc oxide particles which have a specific particle diameter and a specific aspect ratio, and high ultraviolet blocking performance and transparency, and therefore can be suitably used as a cosmetic and a heat releasing material. Provided are hexagonal prism-shaped zinc oxide particles having a primary particle diameter of 0.1 μm or more and less than 0.5 μm and an aspect ratio of less than 2.5.

26 Claims, 10 Drawing Sheets

(51) Int. Cl.
*C30B 29/16* (2006.01)
*C01G 9/02* (2006.01)
*C09C 1/04* (2006.01)
*A61K 8/27* (2006.01)
*A61Q 1/02* (2006.01)
*A61Q 17/04* (2006.01)
*A61K 8/02* (2006.01)

(52) U.S. Cl.
CPC *A61Q 17/04* (2013.01); *C01G 9/02* (2013.01); *C08K 3/22* (2013.01); *C09C 1/043* (2013.01); *C30B 29/16* (2013.01); *C01P 2002/72* (2013.01); *C01P 2004/12* (2013.01); *C01P 2004/40* (2013.01); *C01P 2004/54* (2013.01); *C01P 2004/62* (2013.01); *C08K 2003/2296* (2013.01); *C08K 2201/003* (2013.01); *C08K 2201/016* (2013.01); *Y10T 428/2982* (2015.01)

(56) References Cited

FOREIGN PATENT DOCUMENTS

| | | | |
|---|---|---|---|
| JP | 2008-230895 A | 10/2008 | |
| JP | 2008-254992 A | 10/2008 | |
| JP | WO 2010123142 A1 * | 10/2010 | ............ B82Y 30/00 |
| WO | WO-2010/050430 A1 | 5/2010 | |

OTHER PUBLICATIONS

Meagley et al., "Chemical Control of Crystal Growth with Multidentate Carboxylate Ligands: Effect of Ligand Denticity on Zinc Oxide Crystal Shape", Cryst. Growth Des., 2012, 12, 707-713.

* cited by examiner

FIG. 20

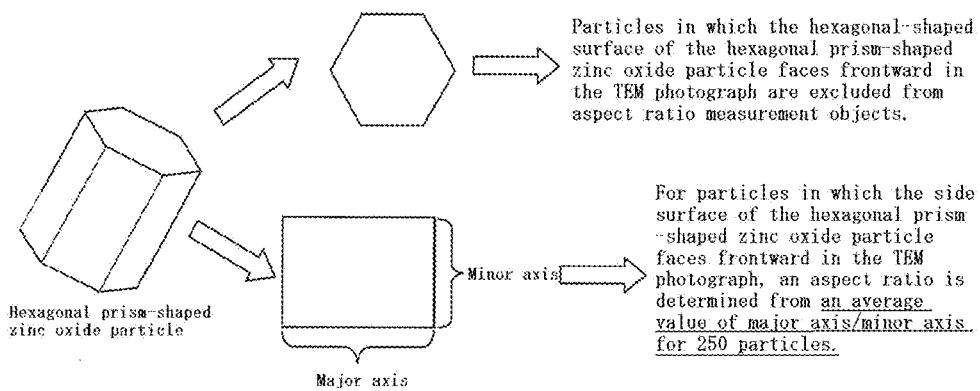

Method for measurement of aspect ratio of hexagonal prism-shaped zinc oxide particles: a major axis and a minor axis are measured for a particle in which the side surface of the hexagonal prism-shaped zinc oxide particle faces frontward in the TEM photograph, and an aspect ratio is determined according to the formula:
aspect ratio = average value of major axis/minor axis for 250 particles.

FIG. 21

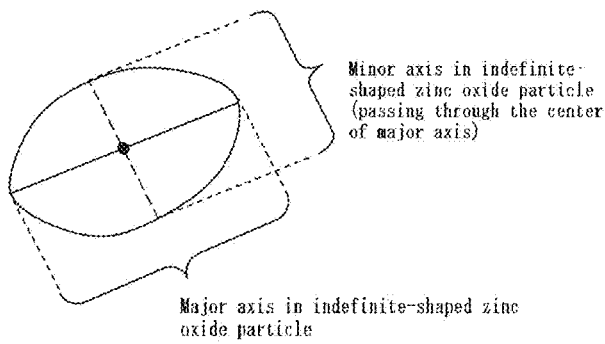

Method for measurement of aspect ratio of zinc oxide particles having an indefinite shape: a major axis and a minor axis passing through the center of the major axis are measured for an indefinite-shaped zinc oxide particle in the TEM photograph, and an aspect ratio is determined according to the formula:
aspect ratio = average value of major axis/minor axis for 250 particles.

FIG. 22
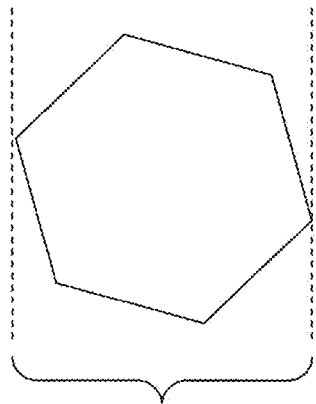
Unidirectional diameter of hexagonal-shaped surface in hexagonal plate-shaped zinc oxide particle: L
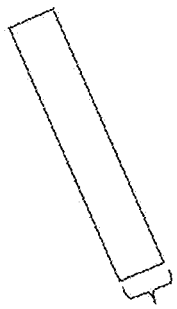
Thickness in hexagonal plate-shaped zinc oxide particle: T
Aspect ratio of hexagonal plate-shaped zinc oxide particles = (average value of unidirectional diameters of hexagonal-shaped surfaces of 250 particles: L)/(average value of thicknesses of 250 particles: T)

HEXAGONAL PRISM-SHAPED ZINC OXIDE PARTICLES, METHOD FOR PRODUCTION OF THE SAME, AND COSMETIC, HEAT RELEASING FILLER, HEAT RELEASING RESIN COMPOSITION, HEAT RELEASING GREASE, AND HEAT RELEASING COATING COMPOSITION COMPRISING THE SAME

CROSS REFERENCE TO RELATED APPLICATIONS

This application is a National Phase filing under 35 U.S.C. §371 of PCT/JP2012/061281 filed on Apr. 26, 2012; and this application claims priority to Application No. 2011-101022 filed in Japan on Apr. 28, 2011, under 35 U.S.C. §119; the entire contents of all are hereby incorporated by reference.

TECHNICAL FIELD

The present invention relates to hexagonal prism-shaped zinc oxide particles, a method for production of the same, and a cosmetic, a heat releasing filler, a heat releasing resin composition, a heat releasing grease and a heat releasing coating composition each containing the same.

BACKGROUND OF THE DISCLOSURE

Zinc oxide particles, which have been used as a sunscreen ultraviolet blocking agent in cosmetic product applications, are ultrafine particles having an average particle diameter of 0.1 µm or less. For example, Patent Documents 1 and 2 disclose zinc oxide fine particles which can be used for ultraviolet blocking agents. However, in the disclosed production methods, particles having a particle diameter of 0.1 µm or more and having both high ultraviolet blocking performance and high transparency cannot be obtained.

On the other hand, some of zinc oxide particles having an average particle diameter of 0.1 µm or more are produced by conventional techniques, but there have been few zinc oxide particles having such a particle diameter and controlled to have a small aspect ratio. Zinc oxide particles having an average particle diameter of 0.1 µm or more and having a large aspect ratio have the disadvantage that high transparency required for sunscreen agents cannot be achieved with stability, and therefore it is desired to develop zinc oxide particles having further excellent properties.

Conventional zinc oxide fine particles having a particle diameter of less than 0.1 µm have the disadvantage that transmitted light increases as particles become smaller, so that the ultraviolet blocking effect at a long wavelength side in a UVA range (wavelength: 315 to 380 nm) is significantly reduced. On the other hand, by increasing the size of zinc oxide particles to 0.1 µm, ultraviolet rays in a UVA range at a longer wavelength side can be blocked as compared to conventional zinc oxide fine particles having a particle diameter of less than 0.1 µm. From such a technical point of view, it is desired to develop zinc oxide particles having a particle diameter of 0.1 µm or more and less than 0.5 µm.

Patent Document 3 describes hexagonal prism- and hexagonal barrel-shaped zinc oxide particles which can be used as a cosmetic. However, in the described production method, hexagonal prism-shaped zinc oxide particles having a particle diameter of less than 0.5 µm cannot be obtained. Further, such zinc oxide particles having a particle diameter of 0.5 µm or more are not preferable because sufficiently high transparency required for sunscreen agents cannot be achieved.

From such a point of view, zinc oxide particles which have a primary particle diameter of 0.1 µm or more and can exhibit higher transparency and higher ultraviolet blocking performance as compared to conventional zinc oxide particles are desired. However, such zinc oxide particles have not been developed.

Zinc oxide particles have a high thermal conductivity, and therefore can be used as a heat releasing filler. As zinc oxide particles having such a property, those having a large particle diameter are often used for increasing the filling rate. However, if the zinc oxide particles can be used in such a manner as to be compounded among particles having a large particle diameter for enhancing thermal conduction as a heat releasing filler, thermal conduction can be more efficiently enhanced.

PRIOR TECHNICAL DOCUMENTS

Patent Documents

[Patent Document 1] Japanese Kokai Publication Hei11-302015
[Patent Document 2] Japanese Kokai Publication Hei3-183620
[Patent Document 3] Japanese Kokai Publication 2008-254992

SUMMARY OF INVENTION

Problems to be Solved by the Invention

In view of the situations described above, it is an object of the present invention to provide zinc oxide particles which have a specific primary particle diameter and a specific aspect ratio, and high ultraviolet blocking performance and transparency, and therefore can be suitably used as a cosmetic and a heat releasing material.

Means for Solving Object

The present invention provides hexagonal prism-shaped zinc oxide particles having a primary particle diameter of 0.1 µm or more and less than 0.5 µm and an aspect ratio of less than 2.5.

The hexagonal prism-shaped zinc oxide particles are preferably those obtained by aging zinc oxide fine particles as a seed in water in which a zinc salt is dissolved.

In the hexagonal prism-shaped zinc oxide particles, the D90/D10 in particle size distribution is preferably 2.4 or less.

The present invention also provides a cosmetic containing the hexagonal prism-shaped zinc oxide particles described above.

The present invention also provides a heat releasing filler made of the hexagonal prism-shaped zinc oxide particles described above.

The present invention also provides a heat releasing resin composition containing the hexagonal prism-shaped zinc oxide particles described above.

The present invention also provides a heat releasing grease containing the hexagonal prism-shaped zinc oxide particles described above.

The present invention also provides a heat releasing coating composition comprising the hexagonal prism-shaped zinc oxide particles described above.

Effects of the Invention

The zinc oxide particles of the present invention have excellent ultraviolet blocking performance as well as excellent transparency, and therefore can be suitably used as an ultraviolet blocking agent for cosmetics. When the zinc oxide particles are used as a heat releasing filler, they exhibit excellent heat releasing performance particularly when used in combination with other heat releasing fillers having a large particle diameter.

BRIEF DESCRIPTION OF THE DRAWINGS

FIG. 20 is an explanatory view for a method for measurement of an aspect ratio of hexagonal prism-shaped zinc oxide particles of the present invention obtained in Examples 1 to 5.

FIG. 21 is an explanatory view for a method for measurement of an aspect ratio of indefinite-shaped zinc oxide particles of comparative examples.

FIG. 22 is an explanatory view for a method for measurement of an aspect ratio of hexagonal plate-shaped zinc oxide particles of comparative examples.

DETAILED DESCRIPTION OF PREFERRED EMBODIMENTS

Figure 1:
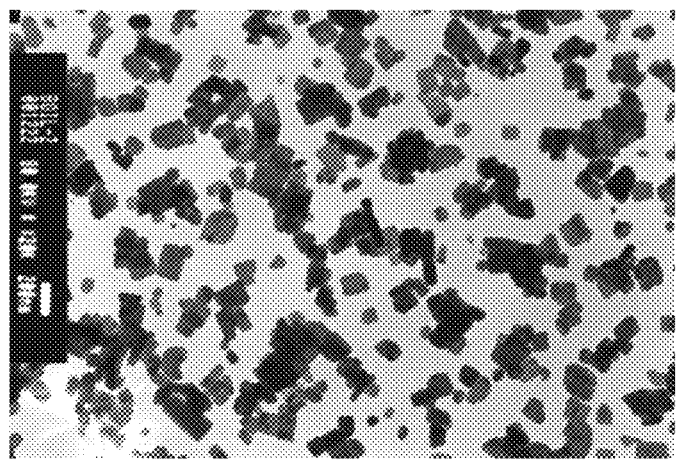
FIG. 1 is a transmission electron microscope photograph of zinc oxide particles of the present invention obtained in Example 1.

The present invention will be described in detail hereinafter.

The present invention provides hexagonal prism-shaped zinc oxide particles having a primary particle diameter of 0.1 μm or more and less than 0.5 μm and an aspect ratio of less than 2.5. Zinc oxide particles having a particle diameter of less than 0.1 μm and large zinc oxide particles having a particle diameter of 0.5 μm or more have been previously known, but zinc oxide particles having a size which is intermediate therebetween have not been known very well. Further, in the present invention, the zinc oxide particles have a hexagonal prism shape with an aspect ratio of less than 2.5.

The present invention provides hexagonal prism-shaped zinc oxide particles having a small aspect ratio and a primary particle diameter of 0.1 μm or more and less than 0.5 μm. By decreasing the aspect ratio as described above, high transparency can be achieved even when the primary particle diameter is 0.1 μm or more and less than 0.5 μm.

The hexagonal prism-shaped zinc oxide particles of the present invention are obtained by crystal-growing zinc oxide fine particles as a seed (seed crystal) in an aqueous zinc acetate solution. By using zinc oxide fine particles as a seed, the primary particle diameter can be arbitrarily controlled. By crystal-growing these zinc oxide fine particles as a seed, hexagonal prism-shaped zinc oxide particles having a small aspect ratio, such as those described above, can be selectively obtained. By forming these zinc oxide particles, particles having both high ultraviolet blocking performance and high transparency can be obtained even when the primary particle diameter is 0.1 μm or more and less than 0.5 μm.

As described above, hexagonal prism-shaped zinc oxide particles are known, but they have a large particle diameter of more than 0.5 μm. However, in order to sufficiently secure transparency and ultraviolet blocking performance by compounding zinc oxide particles in a cosmetic, it is necessary to use the zinc oxide particles of the present invention having a particle diameter of 0.1 μm or more and less than 0.5 μm. Further, in a heat releasing filler, it is very important to increase the filling rate, and for this purpose, it is preferable that particles having a large particle diameter and particles having a smaller particle diameter are used in combination. Therefore, zinc oxide particles having such a specific particle diameter can also be suitably used as a heat releasing filler.

The primary particle diameter herein corresponds to a diameter of a sphere having the same surface area as a specific surface area determined by a BET method. That is, the primary particle diameter is a value determined according to the relational expression:

$$\text{primary particle diameter (μm)} = [6/(Sg \times \rho)]$$

($Sg$ (m$^2$/g): specific surface area, $\rho$ (g/cm$^3$): true specific gravity of particle)

The specific surface area: $Sg$ by the BET method was measured using an fully automatic BET specific surface area measuring device Macsorb (manufactured by Mountech Co., Ltd.), and the measurement value was used for the calculation described above. As the true specific gravity of particle: $\rho$, a value of the true specific gravity of zinc oxide, i.e. 5.6, was used for the above calculation.

Further, the zinc oxide particles of the present invention have a hexagonal prism shape with an aspect ratio of less than 2.5. That is, the zinc oxide particles are hexagonal prism-shaped zinc oxide particles, and particularly when such hexagonal prism-shaped zinc oxide particles having a small aspect ratio are used for a cosmetic, excellent transparency and ultraviolet blocking performance can be achieved. An aspect ratio in the present invention is determined by the following method. For the aspect ratio of the hexagonal prism-shaped zinc oxide particles, a major axis and a minor axis are measured for particles in which the side surface of the hexagonal prism-shaped zinc oxide particle faces frontward (particles observed as a rectangular or square shape) in a visual field of 2000 to 50000 magnification in a transmission electron microscope (TEM, JEM-1200EX II, manufactured by JEOL Ltd.) photograph, and a ratio between the lengths of the major axis and the minor axis: major axis/minor axis is determined. The ratio of major axis/minor axis is measured in the manner described above for 250 hexagonal prism-shaped zinc oxide particles in the TEM photograph, and an average value of a cumulative distribution thereof is determined as an aspect ratio. Hexagonal prism-shaped zinc oxide particles in which the hexagonal-shaped surface faces frontward were excluded from measurement objects because it was difficult to determine the thickness. The method for measurement of an aspect ratio of hexagonal prism-shaped zinc oxide particles is shown in FIG. 20.

The hexagonal prism-shaped zinc oxide particles of the present invention preferably have a D90/D10 of 2.4 or less in particle size distribution. In the above-described parameter, D10 (μm) denotes a 10% cumulative particle diameter on the volume basis, and D90 (μm) denotes a 90% cumulative particle diameter on the volume basis. The D90/D10 is an indicator showing sharpness of the particle size distribution, and the particle size distribution broadens as the D90/D10 becomes larger, while the particle size distribution sharpens as the D90/D10 becomes smaller. That is, when the D90/D10 is 2.4 or less, the number of coarse particles having an extremely large particle diameter is small, the number of fine particles having an extremely small particle diameter is small, and the particle size distribution is sharp. The D90/D10 is more preferably 2.3 or less, further preferably 2.2 or less.

Zinc oxide particles having a sharp particle size distribution are preferable particularly because they are excellent in transparency. For example, when zinc oxide particles satisfy the requirements of the present invention described above for the particle diameter and the aspect ratio, and have a particle size distribution in a specific range as described above, transparency is further improved.

D10 and D90 of zinc oxide particles are values measured by a dynamic light scattering particle diameter distribution measuring device Nanotrack UPA-UT (manufactured by Nikkiso Co., Ltd.). For measurement, zinc oxide particles were dispersed in water, and the dispersion was measured with the refractive index of zinc oxide set at 1.95 and the refractive index of water set at 1.309.

The method for production of zinc oxide particles having the shape described above is not particularly limited, and they can be obtained by, for example, a production method including a step of aging zinc oxide fine particles in water in which a zinc salt is dissolved. Such a method for production of zinc oxide particles is a part of the present invention. This production method has the advantage that zinc oxide particles can be obtained directly without passing through a thermal decomposition step such as that of calcinating. However, calcinating may be performed for the purpose of enhancing crystallinity, and so on.

In this production method, unlike a method of performing aging after forming particles by neutralization of a zinc salt compound as described in the cited documents, zinc oxide fine particles are added as a seed, and therefore particles are grown as the surface layers thereof are repeatedly dissolved and precipitated while zinc oxide fine particles as a seed serve as cores. Thus, the particle diameters of zinc oxide particles obtained after aging using, as a base, zinc oxide fine particles as cores are determined, and particle shapes and particle diameters are established in a uniform state, so that the particle size distribution can be further sharpened. Therefore, the above-mentioned production method is preferable in that the particle diameter and the particle size distribution are more precisely controlled. The production method is also preferable in that owing to zinc oxide fine particles as a seed, zinc oxide particles having a sharp particle size distribution and a small aspect ratio can be selectively obtained.

By adjusting an aging temperature, an aging time, a zinc salt concentration, a zinc oxide fine particle concentration and so on as necessary, the particle diameter and shape, and the like can be adjusted.

In production of hexagonal prism-shaped zinc oxide particles as described above, zinc oxide fine particles are used. The zinc oxide fine particle is not particularly limited, but its particle diameter is preferably 0.01 μm to 0.5 μm. The particle diameter of the zinc oxide fine particle corresponds to a diameter of a sphere having the same surface area as a specific surface area determined by a BET method. That is, the particle diameter is a value determined by the following calculation formula from a specific surface area: Sg determined by making a measurement using a fully automatic BET specific area measuring device Macsorb (manufactured by Mountech Co., Ltd.), and a true specific gravity of zinc oxide: ρ.

particle diameter (μm)=[6/($Sg \times \rho$)]

($Sg$ (m$^2$/g): specific surface area, ρ (g/cm$^3$): true specific gravity of particle)

It is to be noted that as the true specific gravity of particle: ρ, a value of 5.6, which is a value of the true specific gravity of zinc oxide, was used for the above calculation.

Zinc oxide fine particles that can be used as a raw material are not particularly limited, and zinc oxide produced by a known method can be used. Examples of those that are commercially available may include FINEX-75, FINEX-50, FINEX-30, fine zinc oxide, SF-15, Zinc Oxide No. 1, and the like manufactured by Sakai Chemical Industry Co., Ltd.

In the method for production of hexagonal prism-shaped zinc oxide particles according to the present invention, the zinc oxide fine particles are aged in water in which a zinc salt is dissolved.

That is, the zinc oxide fine particles are dispersed in an aqueous zinc salt solution, and heated in this state to be crystal-grown.

The solvent to be used in the present invention is water. Water is inexpensive and safe in terms of handling, and is therefore most preferable from the viewpoint of production control and costs.

The aqueous zinc salt solution to be used is not particularly limited, and examples thereof may include aqueous solutions of zinc acetate, zinc nitrate, zinc sulfate, zinc chloride and zinc formate. Particularly when an aqueous zinc acetate solution, among the aqueous zinc salt solutions, is used, specific hexagonal prism-shaped zinc oxide particles of the present invention can be suitably obtained.

These aqueous zinc salt solutions may be those prepared by mixing zinc oxide, an acid and water to acid-hydrolyze zinc oxide. The particle shape and particle size of zinc oxide to be used when the aqueous zinc salt solution is prepared with zinc oxide, an acid and water are not particularly limited, but the Zn purity of zinc oxide is preferably 95% or more for reducing impurities as much as possible. Examples of the acid include acetic acid, nitric acid, sulfuric acid, hydrochloric acid, formic acid, citric acid, oxalic acid, propionic acid, malonic acid, lactic acid, tartaric acid, gluconic acid and succinic acid, and particularly when acetic acid is used, specific hexagonal prism-shaped zinc oxide particles of the present invention can be suitably obtained. Two of these aqueous zinc salt solutions may be used in combination. The zinc salt concentration in the aqueous zinc salt solution is preferably 0.30 to 0.45 mol/l.

When zinc oxide fine particles are added in the aqueous zinc salt solution to form a slurry, the concentration of zinc oxide fine particles is preferably 10 to 500 g/l based on the total amount of the slurry.

The method for preparation of a slurry is not particularly limited, and for example, a homogeneous slurry having a zinc oxide fine particle concentration of 10 to 500 g/l can be formed by adding the above-described components to water, and dispersing the components at 5 to 30° C. for 10 to 30 minutes.

In the aging described above, components other than zinc oxide fine particles, a zinc salt and water may be added in a small amount within the bounds of not impairing the effect of the present invention. For example, a dispersant and the like may be added.

Preferably, aging is performed at 45 to 110° C. The aging time may be 0.5 to 24 hours. The particle diameter can be adjusted by conditions such as an aging temperature, an aging time, a zinc salt concentration and a zinc oxide fine particle concentration, and therefore it is preferable to appropriately set these conditions according to intended zinc oxide particles.

Hexagonal prism-shaped zinc oxide particles thus obtained may be subjected to post-treatments such as filtration, water washing and drying as necessary.

Hexagonal prism-shaped zinc oxide particles produced by the above-described method may be classified by sieving as necessary. Examples of methods for classification by sieving may include wet classification and dry classification. Further, a treatment such as wet crushing or dry crushing may be performed.

As described above, the method for production of hexagonal prism-shaped zinc oxide particles according to the present invention is capable of obtaining zinc oxide particles without performing a calcinating treatment, but hexagonal prism-shaped zinc oxide particles obtained by the above-described method may be subjected to a calcinating treatment. For calcinating, mention may be made of a known method using an arbitrary device, and treatment conditions and the like are not particularly limited.

The hexagonal prism-shaped zinc oxide particles of the present invention may be further surface-treated as necessary. The surface treatment is not particularly limited, and examples thereof may include known treatment methods such as inorganic surface treatments to form an inorganic oxide layer such as a silica layer, an alumina layer, a zirconia layer or a titania layer, and various kinds of other surface treatments. Two or more kinds of surface treatments may be sequentially performed.

More specific examples of the surface treatment may include surface treatments with a surface treatment agent selected from an organic silicon compound, an organic aluminum compound, an organic titanium compound, a higher fatty acid, a higher fatty acid ester, a metallic soap, a polyhydric alcohol and an alkanolamine. For the surface treatment agent described above, a treatment amount can be appropriately set according to the particle diameter of the zinc oxide particle.

Examples of the organic silicon compound may include organopolysiloxanes such as methyl hydrogen polysiloxane and dimethyl polysiloxane, and silane coupling agents such as triethoxyvinylsilane and diphenyldimethoxysilane.

Examples of the higher fatty acid may include higher fatty acids having 10 to 30 carbon atoms, such as lauric acid, stearic acid and palmitic acid.

Examples of the higher fatty acid ester may include alkyl esters of the above-described higher fatty acids, such as octyl palmitate.

Examples of the metallic soap may include metal salts of the above-described higher fatty acids, such as aluminum stearate and aluminum laurate. The metal species that forms the metallic soap is not particularly limited, and examples thereof may include aluminum, lithium, magnesium, calcium, strontium, barium, zinc and tin.

Examples of the polyhydric alcohol may include trimethylolethane, trimethylolpropane and pentaerythritol.

Examples of the alkanolamine may include diethanolamine, dipropanolamine, triethanolamine and tripropanolamine.

The treatment with the surface treatment agent can be achieved by mixing a predetermined amount of the surface treatment agent with the hexagonal prism-shaped zinc oxide particles. Further, the treatment can be achieved by adding the hexagonal prism-shaped zinc oxide particles to an appropriate medium, for example, water, an alcohol, an ether or the like to be suspended, adding a surface treatment agent to the suspension, followed by stirring, separating, drying and crushing the suspension, or solidifying by evaporation and crushing the suspension.

Since hexagonal prism-shaped zinc oxide particles subjected to the surface treatment described above have various kinds of coating layers on the surfaces thereof, the physiological activity and chemical activity thereof are suppressed when the zinc oxide particles are compounded in a cosmetic, and therefore a particularly excellent cosmetic product can be provided.

The hexagonal prism-shaped zinc oxide particles of the present invention are not particularly limited for applications thereof, and can be suitably used in, for example, applications of raw materials of cosmetics and heat releasing fillers. These cosmetics and heat releasing fillers are a part of the present invention.

A cosmetic containing the hexagonal prism-shaped zinc oxide particles of the present invention has ultraviolet blocking performance and has a small aspect ratio, and is therefore excellent in transparency.

Examples of the cosmetic of the present invention may include a foundation, a makeup base, an eye shadow, a rouge, a mascara, a lipstick and a sunscreen agent. The cosmetic of the present invention can be in any form such as that of an oily cosmetic, an aqueous cosmetic, an O/W type cosmetic or a W/O type cosmetic. Above all, the cosmetic of the present invention can be particularly suitably used in sunscreen agents.

For the cosmetic of the present invention, any aqueous component or oily component that can be used in the field of cosmetics can be used in combination in addition to components that form the above-described mixture. The aqueous component and oily component described above are not particularly limited, and examples thereof may include those containing components such as oils, surfactants, moisturizers, higher alcohols, sequestrants, natural and synthetic polymers, water-soluble and oil-soluble polymers, UV blocking agents, various extracts, inorganic and organic pigments, inorganic and organic clay minerals, inorganic and organic pigments treated with metallic soap or silicone, coloring materials such as organic dyes, preservatives, antioxidants, dyes, thickeners, pH adjusters, perfumes, cooling-sensation agents, antiperspirants, disinfectants, and skin activators. Specifically, a desired cosmetic can be produced in the usual manner using any one or more of the components listed below. The amounts of these components incorporated are not particularly limited as long as they do not interfere with the effects of the present invention.

The oil is not particularly limited, and examples thereof may include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, perilla oil, soybean oil, arachis oil, tea seed oil, kaya oil, rice bran oil, Chinese tung oil, Japanese tung oil, jojoba oil, germ oil, triglycerol, glycerol trioctanoate, glycerol triisopalmitate, cacao butter, coconut oil, horse fat, hydrogenated coconut oil, palm oil, beef tallow, mutton tallow, hydrogenated beef tallow, palm kernel oil, lard, beef bone fat, Japan wax kernel oil, hydrogenated oil, neatsfoot oil, Japan wax, hydrogenated castor oil, beeswax, candelilla wax, cotton wax, carnauba wax, bayberry wax, insect wax, spermaceti wax, montan wax, bran wax, lanolin, kapok wax, lanolin acetate, liquid lanolin, sugarcane wax, isopropyl lanolate, hexyllaurate, reduced lanolin, jojoba wax, hard lanolin, shellac wax, POE lanolin alcohol ether, POE lanolin alcohol acetate, POE cholesterol ether, polyethylene glycol lanolate, POE hydrogenated lanolin alcohol ether, liquid paraffin, ozokerite, pristane, paraffin, ceresin, squalene, Vaseline, and microcrystalline wax.

The lipophilic nonionic surfactant is not particularly limited, and examples thereof may include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; glycerin polyglycerin fatty acids such as glycerol mono-cottonseed oil fatty acid, glycerol monoerucate, glycerol sesquioleate, glycerol monostearate, α,α'-glycerol oleate pyroglutamate, and glycerol monostearate malate; propylene glycol fatty acid esters such as propylene glycol monostearate; hydrogenated castor oil derivatives; and glycerol alkyl ethers.

The hydrophilic nonionic surfactant is not particularly limited, and examples thereof may include POE sorbitan fatty acid esters such as POE sorbitan monostearate, POE sorbitan monooleate and POE sorbitan tetraoleate; POE sorbitol fatty acid esters such as POE sorbitol monolaurate, POE sorbitol monooleate, POE sorbitol pentaoleate and POE sorbitol monostearate; POE glycerin fatty acid esters such as POE glycerin monostearate, POE glycerin monoisostearate and POE glycerin triisostearate; POE fatty acid esters such as POE monooleate, POE distearate, POE monodioleate and ethylene glycol distearate; POE alkyl ethers such as POE lauryl ether, POE oleyl ether, POE stearyl ether, POE behenyl ether, POE 2-octyldodecyl ether and POE cholestanol ether; POE alkyl phenyl ethers such as POE octyl phenyl ether, POE nonyl phenyl ether and POE dinonyl phenyl ether; Pluaronic types such as Pluronic; POE/POP alkyl ethers such as POE/POP cetyl ether, POE/POP 2-decyltetradecyl ether, POE/POP monobutyl ether, POE/POP hydrogenated lanolin and POE/POP glycerin ether; tetra-POE/tetra-POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester and POE hydrogenated castor oil maleic acid; POE beeswax/lanolin derivatives such as POE sorbitol beeswax; alkanolamides such as coconut oil fatty acid diethanolamide, lauric acid monoethanolamide and fatty acid isopropanol amide; POE propylene glycol fatty acid esters; POE alkylamines; POE fatty acid amides; sucrose fatty acid esters; POE nonylphenyl formaldehyde condensation products; alkyl ethoxy dimethylamine oxides; and trioleyl phosphoric acid.

Examples of other surfactants include anionic surfactants such as fatty acid soaps, higher-alkyl sulfuric ester salts, POE triethanolamine lauryl sulfate, and alkyl ether sulfuric ester salts; cationic surfactants such as alkyl trimethylammonium salts, alkyl pyridinium salts, alkyl quaternary ammonium salts, alkyl dimethylbenzyl ammonium salts, POE alkylamines, alkylamine salts, and polyamine fatty acid derivatives; and amphoteric surfactants such as imidazoline amphoteric surfactants and betaine surfactants. They may be incorporated within the bounds of not causing any problems with stability and skin irritation.

The moisturizer is not particularly limited, and examples thereof may include xylitol, sorbitol, maltitol, chondroitin sulfate, hyaluronic acid, mucoitinsulfuric acid, caronic acid, atelocollagen, cholesteryl-12-hydroxystearate, sodium lactate, bile salts, dl-pyrrolidone carboxylate, short-chain soluble collagens, diglycerol (EO) PO adducts, Rosa roxburghii extract, yarrow extract, and melilot extract.

The higher alcohol is not particularly limited, and examples thereof may include linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerol ether (batyl alcohol), 2-decyltetradecynol, lanolin alcohol, cholesterol, phytosterol, hexyldodecanol, isostearyl alcohol, and octyldodecanol.

The sequestrant is not particularly limited, and examples thereof may include 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

The natural water-soluble polymer is not particularly limited, and examples thereof may include plant-derived polymers such as gum arabic, tragacanth gum, galactan, guar gum, carob gum, karaya gum, carrageenan, pectin, agar, quince seed (quince), algal colloid (algal extract), starch (rice, corn, potato, wheat), and glycyrrhizinic acid; microorganism-derived polymers such as xanthan gum, dextran, succinoglucan, and pullulan; and animal-derived polymers such as collagen, casein, albumin, and gelatin.

The semisynthetic water-soluble polymer is not particularly limited, and examples thereof may include starch polymers such as carboxymethyl starch and methyl hydroxypropyl starch; cellulose polymers such as methyl cellulose, nitro cellulose, ethyl cellulose, methyl hydroxypropyl cellulose, hydroxyethyl cellulose, cellulose sodium sulfate, hydroxypropyl cellulose, sodium carboxymethylcellulose (CMC), crystalline cellulose, and cellulose powder; and alginate polymers such as sodium alginate and propylene glycol alginate.

The synthetic water-soluble polymer is not particularly limited, and examples thereof may include vinyl polymers such as polyvinyl alcohol, polyvinyl methyl ether, and polyvinyl pyrrolidone; polyoxyethylene polymers such as polyethylene glycol 20,000, polyethylene glycol 40,000, and polyethylene glycol 60,000; copolymers such as polyoxyethylene-polyoxypropylene copolymers; acrylic polymers such as sodium polyacrylate, polyethylacrylate, and polyacrylamide; polyethyleneimine; and cationic polymers.

The inorganic water-soluble polymer is not particularly limited, and examples thereof may include bentonite, magnesium aluminum silicate (Veegum), laponite, hectorite, and silicic anhydride.

The ultraviolet blocking agent is not particularly limited, and examples thereof may include benzoic acid-based ultraviolet blocking agents such as paraminobenzoic acid (hereinafter, abbreviated as PABA), PABA monoglycerin ester, N,N-dipropoxy PABA ethyl ester, N, N-diethoxy PABA ethyl ester, N,N-dimethyl PABA ethyl ester and N,N-dimethyl PABA butyl ester; anthranilic acid-based ultraviolet blocking agents such as homomethyl-N-acetyl anthranilate; salicylic acid-based ultraviolet blocking agents such as amyl salicylate, menthyl salicylate, homomethyl salicylate, octyl salicylate, phenyl salicylate, benzyl salicylate and p-isopropanol phenyl salicylate; cinnamic acid-based ultraviolet blocking agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate and glycerylmono-2-ethylhexanoyl-di-paramethoxy cinnamate; benzophenone-based ultraviolet blocking agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotriazole, 2-(2'-hydroxy-5'-t-octylphenyl)benzotriazole, 2-(2'-hydroxy-5'-methylphenyl benzotriazole, dibenzalazine, dianisoylmethane, 4-methoxy-4'-t-butyldibenzoylmethane and 5-(3,3-dimethyl-2-norbornylidene)-3-pentane-2-one. Inorganic ultraviolet blocking agents such as titanium oxide particles and zinc oxide particles that do not fall under the present invention can be used in combination.

Other chemical components are not particularly limited, and examples thereof may include vitamins such as vitamin A oil, retinol, retinol palmitate, inositol, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), DL-α-tocopherol, DL-α-tocopherol acetate, pantothenic acid, and biotin; hormones such as estradiol and ethynyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor, sulfur, lysozyme chloride, and pyridoxine chloride.

Various kinds of extracts are not particularly limited, and examples thereof may include *Houttuynia cordata* extract, Phellodendron bark extract, melilot extract, dead nettle extract, licorice extract, peony root extract, soapwort extract, luffa extract, cinchona extract, strawberry geranium extract, sophora root extract, nuphar extract, fennel extract, primrose extract, rose extract, rehmannia root extract, lemon extract, lithospermum root extract, aloe extract, calamus root extract, eucalyptus extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, hamamelis extract, placenta extract, thymic extract, silk extract, and licorice extract.

The hexagonal prism-shaped zinc oxide particles of the present invention can also be used as a heat releasing filler. Preferably, the hexagonal prism-shaped zinc oxide particles of the present invention are used in combination with a heat releasing filler having a different particle diameter when they are used as a filler. The filler that can be used in combination is not particularly limited, and examples thereof may include metal oxides such as magnesium oxide, titanium oxide and aluminum oxide, aluminum nitride, boron nitride, silicon carbide, silicon nitride, titanium nitride, metal silicon and diamond. Further, zinc oxide other than the hexagonal prism-shaped zinc oxide particles described above can be used in combination. The heat releasing filler used in combination may have any shape such as a spherical shape, a needle shape, a rod shape or a plate shape.

When the hexagonal prism-shaped zinc oxide particles of the present invention are used in combination with other heat releasing fillers, the heat releasing filler that can be used in combination preferably has an average particle diameter of 1 to 100 µm. Combination with such a heat releasing filler having a large particle diameter is preferable because the heat releasing filler of the present invention is filled in gaps, so that the filling rate can be increased.

When the hexagonal prism-shaped zinc oxide particles of the present invention are used in combination with zinc oxide particles having a smaller particle diameter and other heat releasing fillers, more excellent heat releasing performance can be achieved.

Preferably, the hexagonal prism-shaped zinc oxide particles of the present invention are contained in a ratio of 10 to 90% by volume based on the total amount of the heat releasing fillers when the hexagonal prism-shaped zinc oxide particles of the present invention are used in combination with other heat releasing fillers. By setting the ratio as described above, the filling rate can be increased.

The zinc oxide particles of the present invention can also be combined with other heat releasing fillers and used as a heat releasing filler composition. Particularly, in the present invention, when the zinc oxide particles are used in combination with other heat releasing fillers, all of combination with a heat releasing filler having a larger particle diameter, combination with a heat releasing filler having a smaller particle diameter and combination with heat releasing fillers having larger and smaller particle diameters are conceivable.

The other heat releasing fillers are not particularly limited, and examples thereof may include metal oxides such as zinc oxide, magnesium oxide, titanium oxide and aluminum oxide, aluminum nitride, boron nitride, silicon carbide, silicon nitride, titanium nitride, metal silicon and diamond. Preferably, the hexagonal prism-shaped zinc oxide particles of the present invention are contained in a ratio of 10 to 90% by volume based on the total amount of the heat releasing composition when used in combination with other heat releasing fillers as described above.

When the hexagonal prism-shaped zinc oxide particles of the present invention are used as a heat releasing filler, they can be mixed with a resin and used as a heat releasing resin composition. In this case, the resin to be used may be either a thermoplastic resin or a thermosetting resin, and examples thereof may include resins such as an epoxy resin, a phenol resin, a polyphenylene sulfide (PPS) resin, a polyester-based resin, polyamide, polyimide, polystyrene, polyethylene, polypropylene, polyvinyl chloride, polyvinylidene chloride, a fluororesin, polymethyl methacrylate, an ethylene/ethyl acrylate copolymer (EEA) resin, polycarbonate, polyurethane, polyacetal, polyphenylene ether, polyether imide, an acrylonitrile-butadiene-styrene copolymer (ABS) resin, a liquid crystal resin (LCP), a silicone resin and an acrylic resin.

The heat releasing resin composition of the present invention may be (1) a resin composition for thermoforming, which is obtained by kneading a thermoplastic resin and the zinc oxide particles in a molten state, (2) a resin composition obtained by kneading a thermosetting resin and the zinc oxide particles, followed by heating the mixture to be cured, or (3) a resin composition for coatings, which is obtained by dispersing the zinc oxide particles in a resin solution or dispersion.

When the heat releasing resin composition of the present invention is a resin composition for thermoforming, a resin component can be freely selected according to a use purpose. For example, when the resin composition is bonded and adhered to a heat source and a radiator plate, a resin having high adhesiveness and a low hardness, such as a silicone resin or an acrylic resin, may be selected.

When the heat releasing resin composition of the present invention is a resin composition for coatings, the resin does not necessarily have to have curability. The coating may be a solvent-based coating containing an organic solvent, or a water-based coating with a resin dissolved or dispersed in water.

When the hexagonal prism-shaped zinc oxide particles are used as a heat releasing filler, they can be mixed with a base oil containing a mineral oil or a synthetic oil, and used as a heat releasing grease. When the hexagonal prism-shaped zinc oxide particles are used as the heat releasing grease, an α-olefin, a diester, a polyol ester, a trimellitic acid ester, a polyphenyl ether, an alkyl phenyl ether or the like can be used as a synthetic oil. The hexagonal prism-shaped zinc oxide particles can also be mixed with a silicone oil and used as a heat releasing grease.

When the hexagonal prism-shaped zinc oxide particles of the present invention are used as a heat releasing filler, other components can also be used in combination. Examples of other components that can be used in combination may include a resin and a surfactant.

The hexagonal prism-shaped zinc oxide particles of the present invention can be used in the fields of vulcanization accelerators for rubber, pigments for coatings/inks, electronic components such as ferrites and varistors, pharmaceuticals and so on in addition to the cosmetics and heat releasing fillers described above.

EXAMPLES

Hereinafter, the present invention will be explained with reference to examples. However, the present invention is not limited to these examples. Herein, descriptions of "part(s)" and "%" mean "part (s) by mass" and "% by mass" unless otherwise specified.

Example 1

Figure 2:
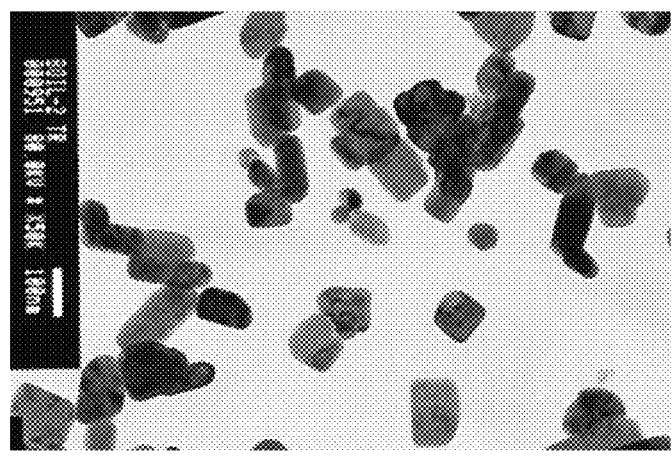
FIG. 2 is a transmission electron microscope photograph of zinc oxide particles of the present invention obtained in Example 1 which are observed with a higher magnification.
Figure 3:
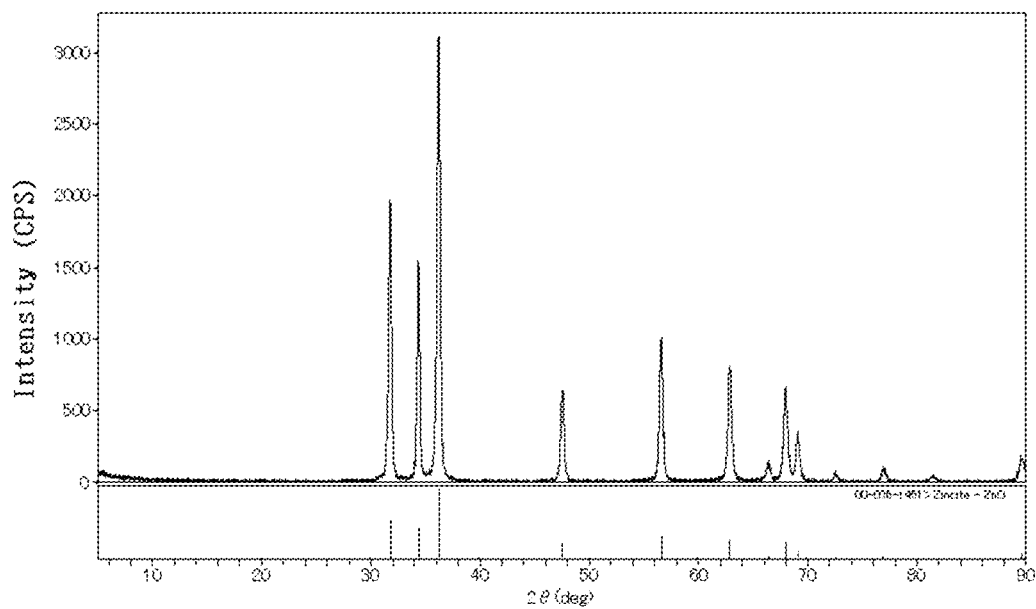
FIG. 3 is an X-ray diffraction spectrum of zinc oxide particles of the present invention obtained in Example 1.

In 1200 ml of an aqueous zinc acetate solution prepared by dissolving 66.51 g of zinc acetate dihydrate (zinc acetate manufactured by Hosoi Chemical Industry Co., Ltd.) in water so as to have a concentration of 0.25 mol/l in terms of zinc acetate dihydrate, 80 g of FINEX-50 (manufactured by Sakai Chemical Industry Co., Ltd., particle diameter: 0.02 μm) was repulped, thereby forming a slurry. Subsequently, the slurry was heated to 100° C. over 60 minutes with stirring, and aged at 100° C. for 7 hours with stirring. After aging, the slurry was filtered, and washed with water. Subsequently, the obtained solid was repulped in 3 liters of water to form a slurry, and the slurry was heated to 100° C. over 60 minutes with stirring, and heated and washed at 100° C. for 30 minutes with stirring. After heating and washing, the slurry was filtered, washed with water, and dried at 110° C. for 12 hours to obtain hexagonal prism-shaped zinc oxide particles having a primary particle diameter of 0.10 μm. The size and form of the obtained particles were observed with a transmission electron microscope (TEM, JEM-1200EX II, manufactured by JEOL Ltd.). The obtained electron microscope photograph is shown in FIG. 1. Further, an electron microscope photograph with a higher magnification is shown in FIG. 2. Further, the X-ray diffraction spectrum of the obtained particles is shown in FIG. 3. The results of evaluating the physical properties of the obtained particles and the physical properties of the coating film are shown in Table 1.

Example 2

Figure 4:
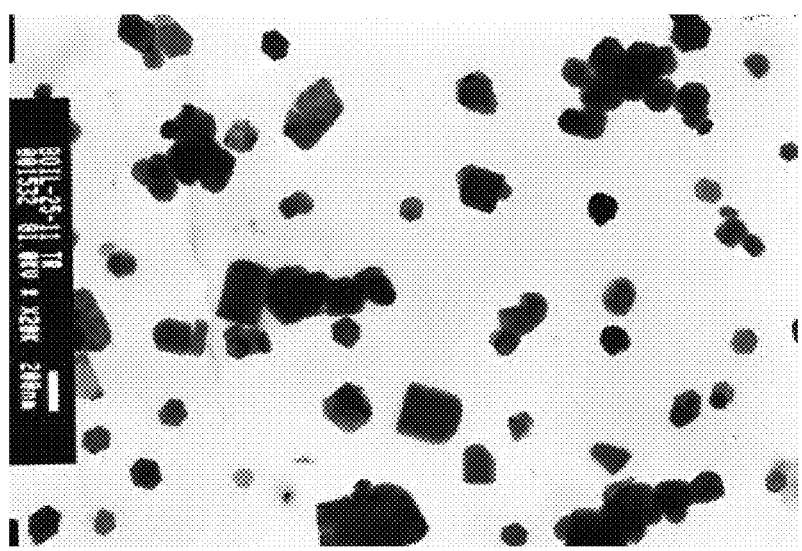
FIG. 4 is a transmission electron microscope photograph of zinc oxide particles of the present invention obtained in Example 2.
Figure 5:
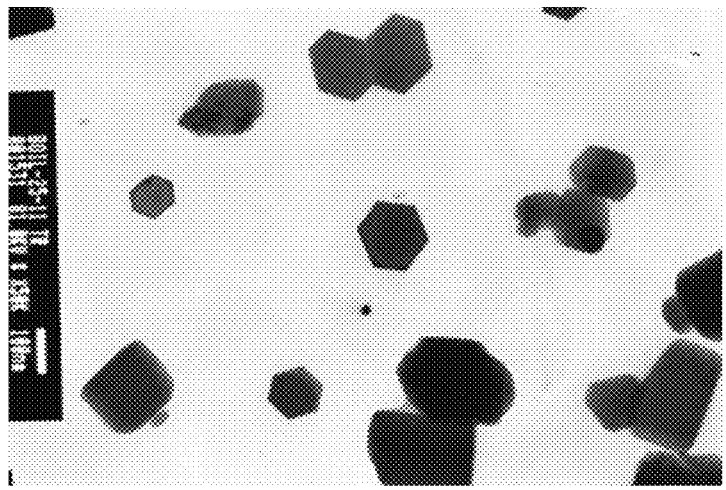
FIG. 5 is a transmission electron microscope photograph of zinc oxide particles of the present invention obtained in Example 2 which are observed with a higher magnification.

In 1200 ml of an aqueous zinc acetate solution prepared by dissolving 133.02 g of zinc acetate dihydrate (zinc acetate manufactured by Hosoi Chemical Industry Co., Ltd.) in water so as to have a concentration of 0.5 mol/l in terms of zinc acetate dihydrate, 80 g of SF-15 (manufactured by Sakai Chemical Industry Co., Ltd., particle diameter: 0.08 μm) was repulped, thereby forming a slurry. Subsequently, the slurry was heated to 70° C. over 42 minutes with stirring, and aged at 70° C. for 3 hours with stirring. After aging, the slurry was filtered, and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain hexagonal prism-shaped zinc oxide particles having a primary particle diameter of 0.19 μm. The size and form of the obtained particles were observed with a transmission electron microscope (TEM, JEM-1200EX II, manufactured by JEOL Ltd.). The obtained electron microscope photograph is shown in FIG. 4. Further, an electron microscope photograph with a higher magnification is shown in FIG. 5. The results of evaluating the physical properties of the obtained particles and the physical properties of the coating film are shown in Table 1.

Example 3

Figure 6:
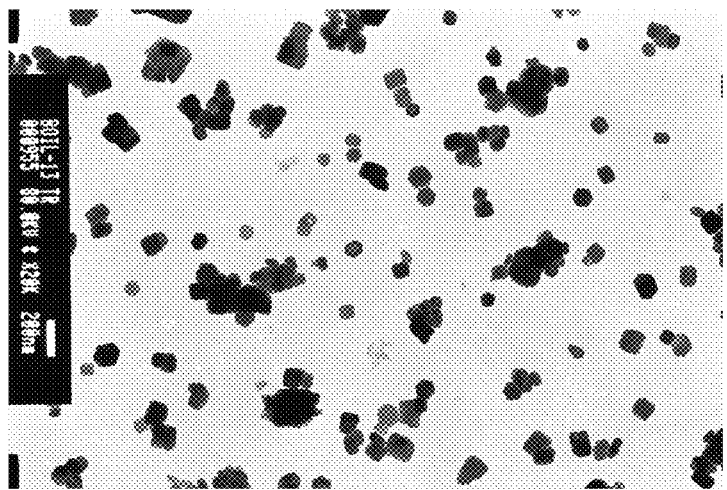
FIG. 6 is a transmission electron microscope photograph of zinc oxide particles of the present invention obtained in Example 3.
Figure 7:
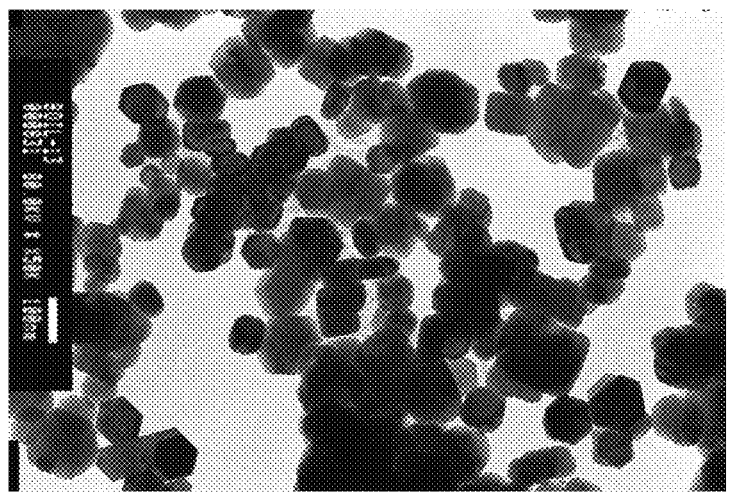
FIG. 7 is a transmission electron microscope photograph of zinc oxide particles of the present invention obtained in Example 3 which are observed with a higher magnification.
Figure 8:
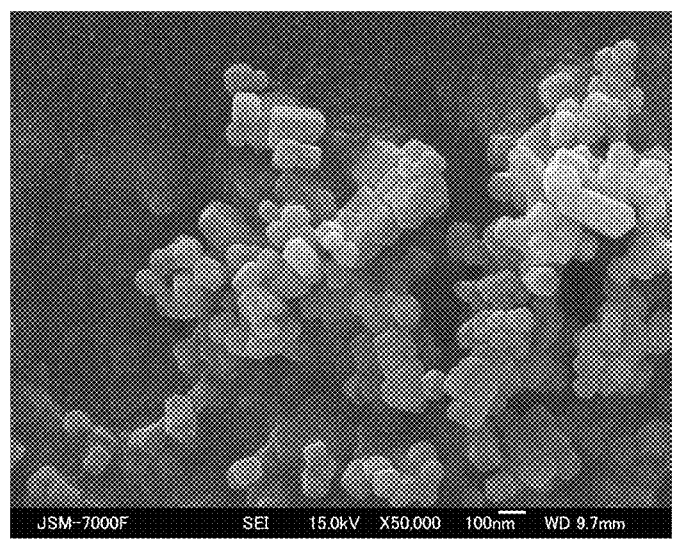
FIG. 8 is a scanning electron microscope photograph of zinc oxide particles of the present invention obtained in Example 3.
Figure 9:
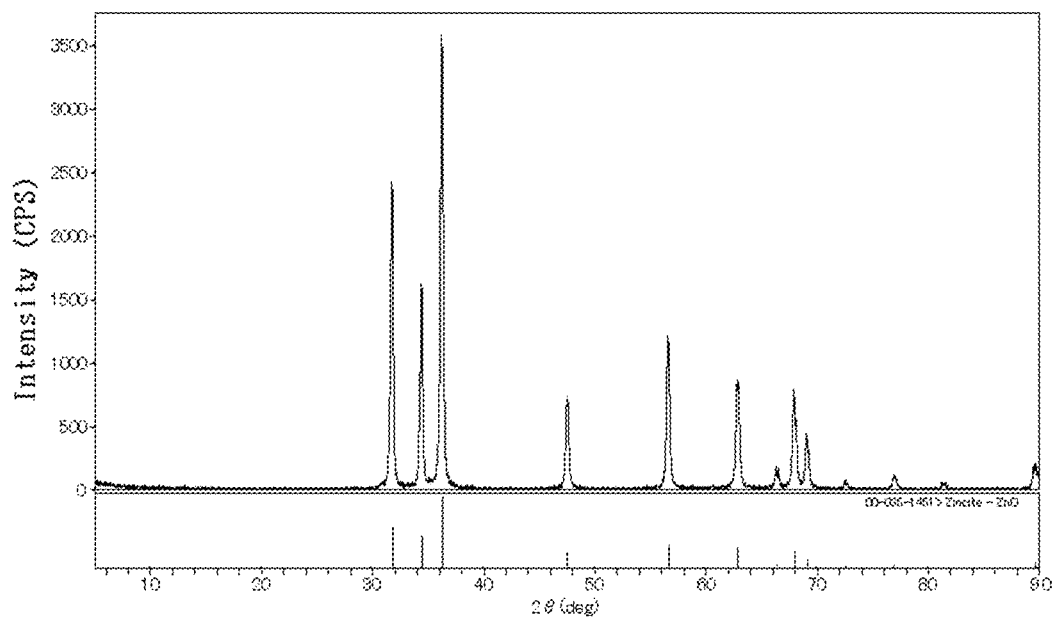
FIG. 9 is an X-ray diffraction spectrum of zinc oxide particles of the present invention obtained in Example 3.

In 1200 ml of an aqueous zinc acetate solution prepared by dissolving 106.42 g of zinc acetate dihydrate (zinc acetate manufactured by Hosoi Chemical Industry Co., Ltd.) in water so as to have a concentration of 0.4 mol/l in terms of zinc acetate dihydrate, 80 g of SF-15 (manufactured by Sakai Chemical Industry Co., Ltd., particle diameter: 0.08 μm) was repulped, thereby forming a slurry. Subsequently, the slurry was heated to 70° C. over 42 minutes with stirring, and aged at 70° C. for 5 hours with stirring. After aging, the slurry was filtered, and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain hexagonal prism-shaped zinc oxide particles having a primary particle diameter of 0.13 μm. The size and form of the obtained particles were observed with a transmission electron microscope (TEM, JEM-1200EX II, manufactured by JEOL Ltd.). The obtained electron microscope photograph is shown in FIG. 6. Further, an electron microscope photograph with a higher magnification is shown in FIG. 7. The size and form of the obtained particles were observed with a scanning electron microscope (SEM, JSM-7000F, manufactured by JEOL Ltd.). The obtained electron microscope photograph is shown in FIG. 8. Further, the X-ray diffraction spectrum of the obtained particles is shown in FIG. 9. The results of evaluating the physical properties of the obtained particles and the physical properties of the coating film are shown in Table 1.

Example 4

Figure 10:
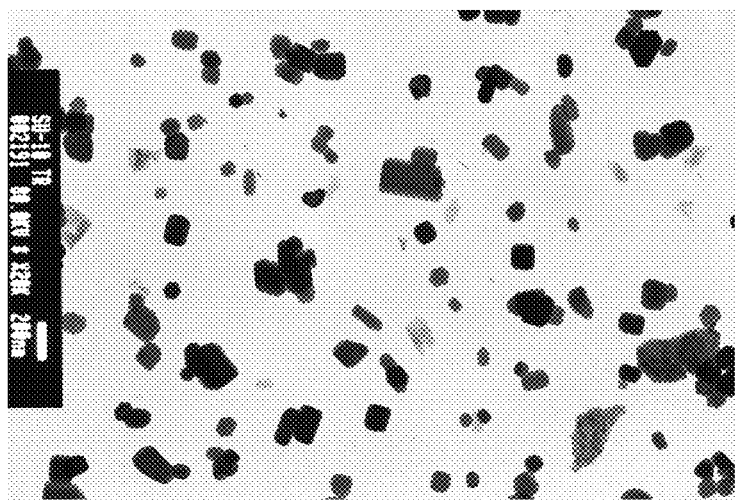
FIG. 10 is a transmission electron microscope photograph of zinc oxide particles of the present invention obtained in Example 4.
Figure 11:
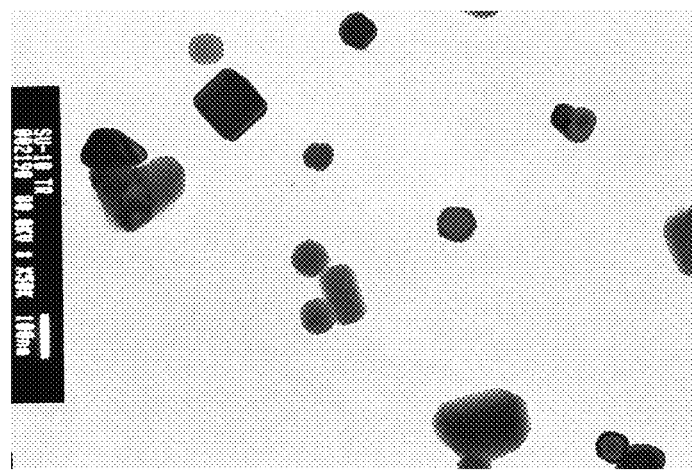
FIG. 11 is a transmission electron microscope photograph of zinc oxide particles of the present invention obtained in Example 4 which are observed with a higher magnification.

In 1200 ml of an aqueous zinc acetate solution prepared by dissolving 106.42 g of zinc acetate dihydrate (zinc acetate manufactured by Hosoi Chemical Industry Co., Ltd.) in water so as to have a concentration of 0.4 mol/l in terms of zinc acetate dihydrate, 80 g of SF-15 (manufactured by Sakai Chemical Industry Co., Ltd., particle diameter: 0.08 μm) was repulped, thereby forming a slurry. Subsequently, the slurry was heated to 90° C. over 54 minutes with stirring, and aged at 90° C. for 7 hours with stirring. After aging, the slurry was filtered, and washed with water. Subsequently, the obtained solid was repulped in 3 liters of water to form a slurry, and the slurry was heated to 90° C. over 54 minutes with stirring, and heated and washed at 90° C. for 30 minutes with stirring. After heating and washing, the slurry was filtered, washed with water, and dried at 110° C. for 12 hours to obtain hexagonal prism-shaped zinc oxide particles having a primary particle diameter of 0.15 μm. The size and form of the obtained particles were observed with a transmission electron microscope (TEM, JEM-1200EX II, manufactured by JEOL Ltd.). The obtained electron microscope photograph is shown in FIG. 10. Further, an electron microscope photograph with a higher magnification is shown in FIG. 11. The results of evaluating the physical properties of the obtained particles and the physical properties of the coating film are shown in Table 1.

Example 5

Figure 12:
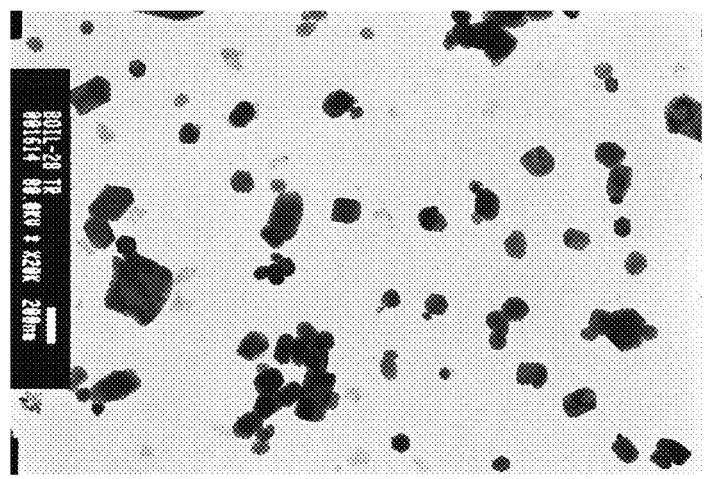
FIG. 12 is a transmission electron microscope photograph of zinc oxide particles of the present invention obtained in Example 5.
Figure 13:
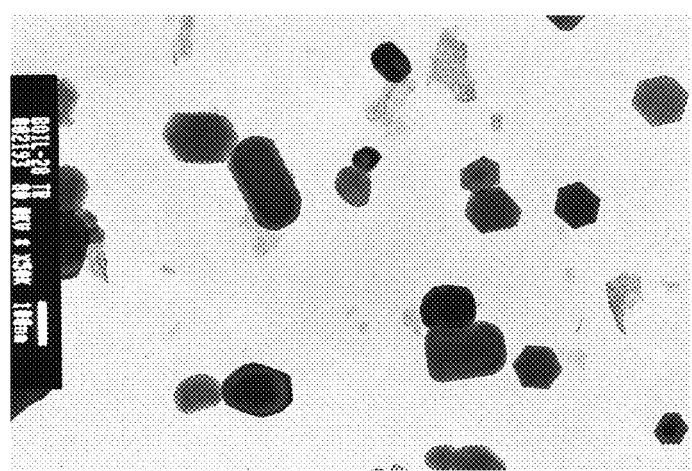
FIG. 13 is a transmission electron microscope photograph of zinc oxide particles of the present invention obtained in Example 5 which are observed with a higher magnification.

In 1200 ml of an aqueous zinc acetate solution prepared by dissolving 106.42 g of zinc acetate dihydrate (zinc acetate manufactured by Hosoi Chemical Industry Co., Ltd.) in water so as to have a concentration of 0.4 mol/l in terms of zinc acetate dihydrate, 80 g of FINEX-30 (manufactured by Sakai Chemical Industry Co., Ltd., particle diameter: 0.04 μm) was repulped, thereby forming a slurry. Subsequently, the slurry was heated to 70° C. over 42 minutes with stirring, and aged at 70° C. for 3 hours with stirring. After aging, the slurry was filtered, and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain hexagonal prism-shaped zinc oxide particles having a primary particle diameter of 0.11 μm. The size and form of the obtained particles were observed with a transmission electron microscope (TEM, JEM-1200EX II, manufactured by JEOL Ltd.). The obtained electron microscope photograph is shown in FIG. 12. Further, an electron microscope photograph with a higher magnification is shown in FIG. 13. The results of evaluating the physical properties of the obtained particles and the physical properties of the coating film are shown in Table 1.

Comparative Example 1

Figure 14:
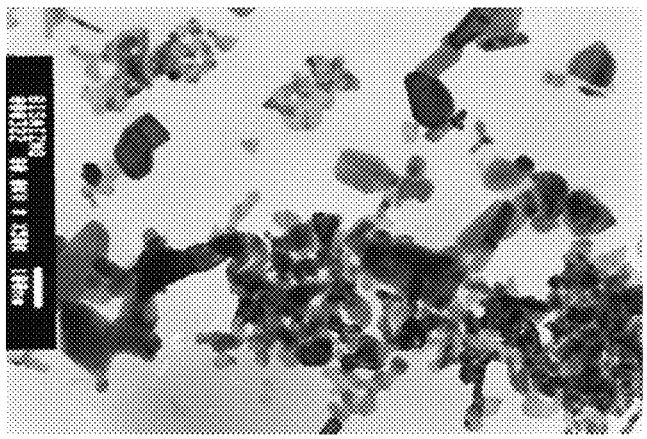
FIG. 14 is a transmission electron microscope photograph of zinc oxide particles (Fine zinc oxide manufactured by Sakai Chemical Industry Co., Ltd.) used in Comparative Example 1.

Fine zinc oxide (manufactured by Sakai Chemical Industry Co., Ltd., particle diameter: 0.11 μm) was evaluated in the same manner as in examples. The electron microscope photograph is shown in FIG. 14. The results of evaluating the physical properties of the obtained particles and the physical properties of the coating film are shown in Table 1.

Comparative Example 2

Figure 15:
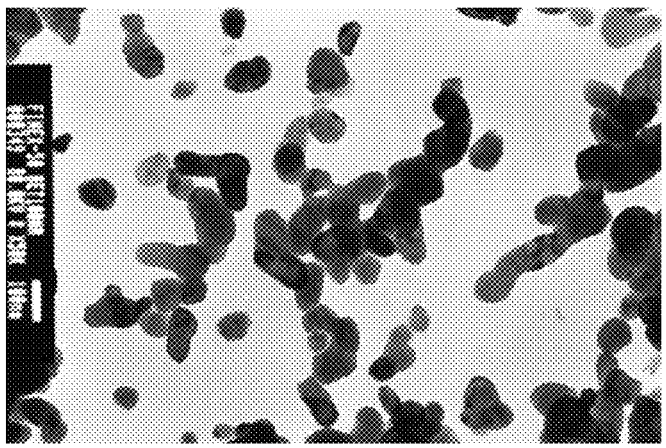
FIG. 15 is a transmission electron microscope photograph of zinc oxide particles obtained in Comparative Example 2.

In an alumina crucible (length/width/height=100 mm/100 mm/35 mm) was put 10 g of FINEX-50 (manufactured by Sakai Chemical Industry Co., Ltd., particle diameter: 0.02 μm), and left standing and calcinated at 525° C. for 2 hours in an electric muffle furnace (manufactured by TOYO ENGINEERING WORKS, LTD.) to obtain indefinite-shaped zinc oxide particles having a primary particle diameter of 0.10 μm. The size and form of the obtained particles were observed with a transmission electron microscope (TEM, JEM-1200EX II, manufactured by JEOL Ltd.). The obtained electron microscope photograph is shown in FIG. 15. The results of evaluating the physical properties of the obtained particles and the physical properties of the coating film are shown in Table 1.

Comparative Example 3

Figure 16:
FIG. 16 is a transmission electron microscope photograph of zinc oxide particles (FINEX-50 manufactured by Sakai Chemical Industry Co., Ltd.) used in Comparative Example 3.

FINEX-50 (manufactured by Sakai Chemical Industry Co., Ltd., particle diameter: 0.02 μm) was evaluated in the same manner as in the examples. The electron microscope photograph is shown in FIG. 16. The results of evaluating the physical properties of the obtained particles and the physical properties of the coating film are shown in Table 1.

Comparative Example 4

Figure 17:
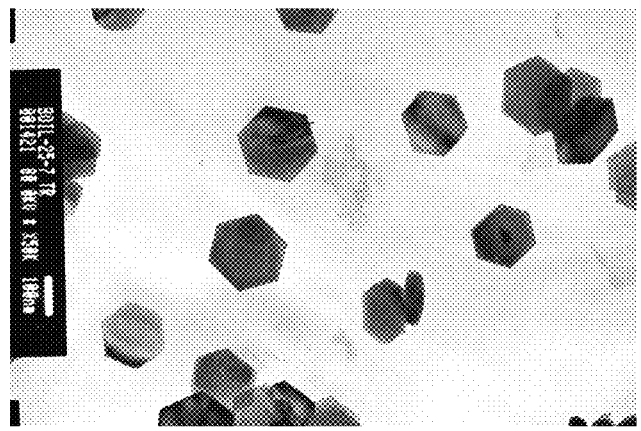
FIG. 17 is a transmission electron microscope photograph of zinc oxide particles obtained in Comparative Example 4.

In 1200 ml of an aqueous zinc acetate solution prepared by dissolving 133.02 g of zinc acetate dihydrate (zinc acetate manufactured by Hosoi Chemical Industry Co., Ltd.) in water so as to have a concentration of 0.5 mol/l in terms of zinc acetate dihydrate, 80 g of FINEX-50 (manufactured by Sakai Chemical Industry Co., Ltd., particle diameter: 0.02 μm) was repulped, thereby forming a slurry. Subsequently, the slurry was heated to 70° C. over 42 minutes with stirring, and aged at 70° C. for 3 hours with stirring. After aging, the slurry was quenched immediately, then filtered and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain hexagonal plate-shaped zinc oxide particles having a primary particle diameter of 0.11 µm. The size and form of the obtained particles were observed with a transmission electron microscope (TEM, JEM-1200EX II, manufactured by JEOL Ltd.). The obtained electron microscope photograph is shown in FIG. 17. The results of evaluating the physical properties of the obtained particles and the physical properties of the coating film are shown in Table 1.

Comparative Example 5

Figure 18:
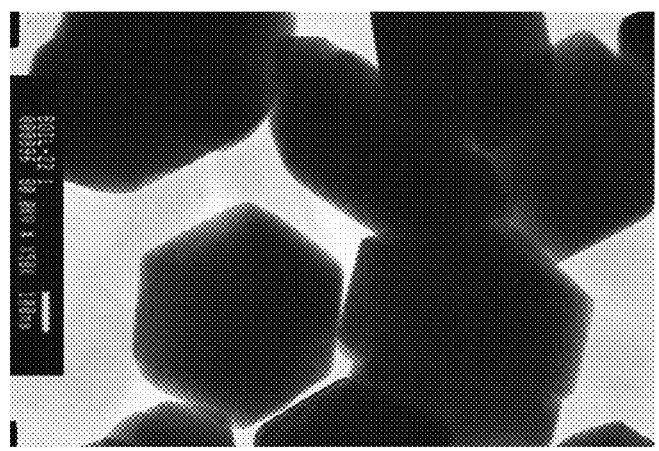
FIG. 18 is a transmission electron microscope photograph of zinc oxide particles obtained in Comparative Example 5.

In 1200 ml of an aqueous zinc acetate solution prepared by dissolving 266.05 g of zinc acetate dihydrate (zinc acetate manufactured by Hosoi Chemical Industry Co., Ltd.) in water so as to have a concentration of 1.0 mol/l in terms of zinc acetate dihydrate, 80 g of SF-15 (manufactured by Sakai Chemical Industry Co., Ltd., particle diameter: 0.08 µm) was repulped, thereby forming a slurry. Subsequently, the slurry was heated to 90° C. over 54 minutes with stirring, and aged at 90° C. for 7 hours with stirring. After aging, the slurry was filtered, and washed with water. Subsequently, the obtained solid was repulped in 3 liters of water to form a slurry, and the slurry was heated to 90° C. over 54 minutes with stirring, and heated and washed at 90° C. for 30 minutes with stirring. After heating and washing, the slurry was filtered, washed with water, and dried at 110° C. for 12 hours to obtain indefinite-shaped zinc oxide particles having a primary particle diameter of 0.65 µm, which partially included hexagonal plate-shaped particles. The size and form of the obtained particles were observed with a transmission electron microscope (TEM, JEM-1200EX II, manufactured by JEOL Ltd.). The obtained electron microscope photograph is shown in FIG. 18. The results of evaluating the physical properties of the obtained particles and the physical properties of the coating film are shown in Table 1.

Comparative Example 6

Figure 19:
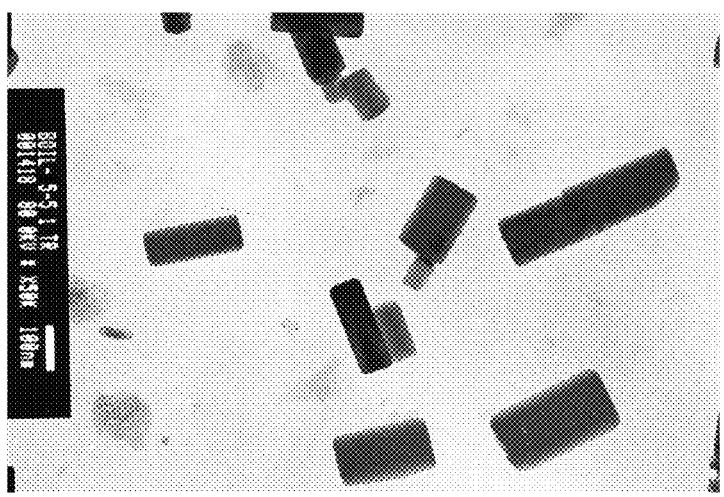
FIG. 19 is a transmission electron microscope photograph of zinc oxide particles obtained in Comparative Example 6.

In 1200 ml of an aqueous zinc acetate solution prepared by dissolving 53.21 g of zinc acetate dihydrate (zinc acetate manufactured by Hosoi Chemical Industry Co., Ltd.) in water so as to have a concentration of 0.2 mol/l in terms of zinc acetate dihydrate, 80 g of SF-15 (manufactured by Sakai Chemical Industry Co., Ltd., particle diameter: 0.08 µm) was repulped, thereby forming a slurry. Subsequently, the slurry was heated to 70° C. over 42 minutes with stirring, and aged at 70° C. for 3 hours with stirring. After aging, the slurry was filtered, and washed with water. Subsequently, the obtained solid was repulped in 3 liters of water to form a slurry, and the slurry was heated to 70° C. over 42 minutes with stirring, and heated and washed at 70° C. for 30 minutes with stirring. After heating and washing, the slurry was filtered, washed with water, and dried at 110° C. for 12 hours to obtain rod-shaped zinc oxide particles having a primary particle diameter of 0.22 µm. The size and form of the obtained particles were observed with a transmission electron microscope (TEM, JEM-1200EX II, manufactured by JEOL Ltd.). The obtained electron microscope photograph is shown in FIG. 19. The results of evaluating the physical properties of the obtained particles and the physical properties of the coating film are shown in Table 1.

(Composition of Obtained Particles)

The X-ray diffraction spectra shown in FIGS. 3 and 9 and the compositions of the obtained particles in Table 1 show results of performing analysis using an X-ray diffractometer UltimaIII (manufactured by Rigaku Corporation) having an X-ray tube with copper.

(Aspect Ratio)

The aspect ratio of the hexagonal prism-shaped zinc oxide particles of the examples was measured by the measurement method described above.

For the aspect ratio of the zinc oxide particles having an indefinite particle shape in comparative examples, a major axis of the indefinite-shaped zinc oxide particle and a minor axis passing through the center of the major axis are measured in a visual field of 2000 to 50000 magnification in a transmission electron microscope (TEM, JEM-1200EX II, manufactured by JEOL Ltd.) photograph, and a ratio between the lengths of the major axis and the minor axis: major axis/minor axis is determined. The ratio of major axis/minor axis is measured in the manner described above for 250 indefinite-shaped zinc oxide particles in the TEM photograph, and an average value of a cumulative distribution thereof is determined as an aspect ratio. The method for measurement of an aspect ratio of indefinite-shaped zinc oxide particles is shown in FIG. 21.

The aspect ratio of the zinc oxide particles having a hexagonal plate particle shape in the comparative examples is a value determined as a ratio of L/T where L is an average value of measured particle diameters (µm) of 250 particles, the particle diameter defined by a unidirectional diameter for particles in which the hexagonal-shaped surface of the hexagonal plate-shaped zinc oxide particle faces frontward (distance between two parallel lines in a fixed direction with a particle held therebetween; measurements are made in a fixed direction for particles in which the hexagonal-shaped surface on the image faces frontward), and T is an average value of measured thicknesses (µm) (length of the shorter side of rectangle) of 250 particles for particles in which the side surface of the hexagonal plate-shaped zinc oxide particle faces frontward (particles that appear rectangular), in a visual field of 2000 to 50000 magnification in a transmission electron microscope (TEM, JEM-1200EX II, manufactured by JEOL Ltd.) photograph or a scanning electron microscope (SEM, JSM-5600, manufactured by JEOL Ltd.) photograph. For the method for measurement of an aspect ratio, FIG. 22 is attached.

(D50, D90, D10, D90/D10)

Herein, D50 (µm), D90 (µm) and D10 (µm) are values measured by a dynamic light scattering particle diameter distribution measuring device Nanotrack UPA-UT (manufactured by Nikkiso Co., Ltd.). The zinc oxide particles of each of examples and comparative examples were dispersed in water, and the dispersion was measured with the refractive index of zinc oxide set at 1.95 and the refractive index of water set at 1.309. D50 (µm) denotes a 50% cumulative particle diameter on the volume basis, D90 (µm) denotes a 90% cumulative particle diameter on the volume basis, and D10 (µm) denotes a 10% cumulative particle diameter on the volume basis. A ratio of D90/D10 is calculated as an indicator of sharpness of the particle size distribution. The particle size distribution broadens as the value becomes larger, while the particle size distribution sharpens as the value becomes smaller.

(Preparation of Coating Film)

In a mayonnaise bottle having a volume of 75 ml, 2 g of zinc oxide particles obtained in each of examples and comparative examples described above, 10 g of varnish (ACRYDIC A-801-P manufactured by DIC Corporation), 5 g of butyl acetate (special grade reagent, manufactured by Wako Pure Chemical Industries, Ltd.), 5 g of xylene (genuine special grade, manufactured by JUNSEI CHEMICAL CO., LTD.) and 38 g of glass beads (1.5 mm, manufactured by Potters-Ballotini Co., Ltd.) were put and sufficiently mixed, then fixed in a paint conditioner Model 5410 (manufactured by RED DEVIL, Inc.), and subjected to a dispersion treatment by giving vibrations for 90 minutes, thereby preparing a coating. Next, a small amount of the prepared coating was added dropwise onto a slide glass (length/width/thickness=76 mm/26 mm/0.8 to 1.0 mm, manufactured by Matsunami Glass Ind., Ltd.), and a coating film was prepared using a bar coater (No. 579 ROD No. 6, manufactured by YASUDA SEIKI SEISAKUSHO, LTD.). The prepared coating film was dried at 20° C. for 12 hours, and then used for measurement of total light transmittance 1, total light transmittance 2, total light transmittance 3, parallel light transmittance 1 and parallel light transmittance 2.

(Total Light Transmittance 1, Total Light Transmittance 2, Total Light Transmittance 3, Parallel Light Transmittance 1 and Parallel Light Transmittance 2)

Herein, total light transmittance 1(%), total light transmittance 2(%), total light transmittance 3(%), parallel light transmittance 1(%) and parallel light transmittance 2(%) are values obtained by measuring the prepared coating film using a spectrophotometer V-570 (manufactured by JASCO Corporation). The value of total light transmittance 1(%) is a value of total light transmittance at a wavelength of 310 nm, the value of total light transmittance 2(%) is a value of total light transmittance at a wavelength of 350 nm, the value of total light transmittance 3(%) is a value of total light transmittance at a wavelength of 375 nm, the value of parallel light transmittance 1(%) is a value of parallel light transmittance at a wavelength of 500 nm, and the value of parallel light transmittance 2(%) is a value of parallel light transmittance at a wavelength of 700 nm. An ultraviolet blocking effect to ultraviolet rays having a wavelength of UVB is enhanced as the value of total light transmittance 1(%) becomes smaller, and an ultraviolet blocking effect to ultraviolet rays having a wavelength of UVA is enhanced as the values of total light transmittance 2(%) and total light transmittance 3(%) become smaller. Particularly, when the value of total light transmittance 3(%) is small, a blocking region to ultraviolet rays having a wavelength of UVA extends over a wider range. Visible light transparency is enhanced as the values of parallel light transmittance 1(%) and parallel light transmittance 2(%) become larger.

TABLE 1

| | | Example 1 | Example 2 | Example 3 | Example 4 | Example 5 | Comparative Example 1 | Comparative Example 2 |
|---|---|---|---|---|---|---|---|---|
| Preparation conditions | Zinc oxide fine particles as raw material | FINEX-50 | SF-15 | SF-15 | SF-15 | FINEX-30 | Fine zinc oxide | FINEX-50 |
| | Particle diameter of raw material (μm) | 0.02 | 0.08 | 0.08 | 0.08 | 0.04 | 0.11 | 0.02 |
| | Amount of raw material used in preparation (g) | 80 | 80 | 80 | 80 | 80 | | |
| | Zinc salt used in preparation | Zinc acetate dihydrate | Zinc acetate dihydrate | Zinc acetate dihydrate | Zinc acetate dihydrate | Zinc acetate dihydrate | | |
| | Amount of zinc salt (g) | 66.51 | 133.02 | 106.42 | 106.42 | 106.42 | | |
| | Solvent used in preparation | Water | Water | Water | Water | Water | | |
| | Amount of zinc salt solution (ml) | 1200 | 1200 | 1200 | 1200 | 1200 | | |
| | Concentration of zinc salt solution (mol/l) | 0.25 | 0.5 | 0.4 | 0.4 | 0.4 | | |
| | Aging temperature (° C.) | 100 | 70 | 70 | 90 | 70 | | |
| | Aging time (Hr) | 7 | 3 | 5 | 7 | 3 | | |
| | Calcinating temperature/ calcinating time | | | | | | | 525° C./ 2 Hr |
| Physical properties of particles | Composition of obtained particles | Zinc oxide | Zinc oxide | Zinc oxide | Zinc oxide | Zinc oxide | Zinc oxide | Zinc oxide |
| | Particle shape | Hexagonal prism shape | Hexagonal prism shape | Hexagonal prism shape | Hexagonal prism shape | Hexagonal prism shape | Indefinite shape | Indefinite shape |
| | Primary particle diameter (μm) | 0.10 | 0.19 | 0.13 | 0.15 | 0.11 | 0.11 | 0.10 |
| | D50 (μm) | 0.18 | 0.40 | 0.20 | 0.19 | 0.15 | 0.23 | 0.17 |
| | D90 (μm) | 0.24 | 0.54 | 0.25 | 0.27 | 0.21 | 0.41 | 0.37 |
| | D10 (μm) | 0.13 | 0.25 | 0.15 | 0.13 | 0.10 | 0.17 | 0.09 |
| | D90/D10 | 1.92 | 2.16 | 1.67 | 2.09 | 2.09 | 2.47 | 4.05 |
| | Aspect ratio | 1.4 | 1.6 | 1.2 | 1.4 | 1.3 | 2.1 | 1.9 |
| Physical properties of coating film | Total light transmittance 1 (%) | 14 | 20 | 12 | 16 | 15 | 20 | 15 |
| | Total light transmittance 2 (%) | 12 | 18 | 10 | 14 | 15 | 17 | 14 |
| | Total light transmittance 3 (%) | 15 | 23 | 10 | 11 | 15 | 19 | 18 |
| | Parallel light transmittance 1 (%) | 71 | 63 | 56 | 55 | 65 | 53 | 57 |
| | Parallel light transmittance 2 (%) | 90 | 85 | 81 | 80 | 86 | 79 | 81 |

| | | | Comparative Example 3 | Comparative Example 4 | Comparative Example 5 | Comparative Example 6 |
|---|---|---|---|---|---|---|
| | Preparation conditions | Zinc oxide fine particles as raw material | FINEX-50 | FINEX-50 | SF-15 | SF-15 |
| | | Particle diameter of raw material (μm) | 0.02 | 0.02 | 0.08 | 0.02 |
| | | Amount of raw material used in preparation (g) | | 80 | 80 | 80 |

TABLE 1-continued

|  |  |  |  |  |  |
|---|---|---|---|---|---|
|  | Zinc salt used in preparation | Zinc acetate dihydrate | Zinc acetate dihydrate | Zinc acetate dihydrate |  |
|  | Amount of zinc salt (g) | 133.02 | 266.05 | 53.21 |  |
|  | Solvent used in preparation | Water | Water | Water |  |
|  | Amount of zinc salt solution (ml) | 1200 | 1200 | 1200 |  |
|  | Concentration of zinc salt solution (mol/l) | 0.5 | 1.0 | 0.2 |  |
|  | Aging temperature (° C.) | 70 | 90 | 70 |  |
|  | Aging time (Hr) | 3 | 7 | 3 |  |
|  | Calcinating temperature/ calcinating time |  |  |  |  |
| Physical properties of particles | Composition of obtained particles | Zinc oxide | Zinc oxide | Zinc oxide | Zinc oxide |
|  | Particle shape | Indefinite shape | Hexagonal plate shape | Hexagonal olate shape + indefinite shape | Rod shape |
|  | Primary particle diameter (μm) | 0.02 | 0.11 | 0.65 | 0.22 |
|  | D50 (μm) | 0.14 | 0.15 | 0.70 | 0.23 |
|  | D90 (μm) | 0.41 | 0.28 | 1.28 | 0.44 |
|  | D10 (μm) | 0.05 | 0.11 | 0.46 | 0.15 |
|  | D90/D10 | 7.39 | 2.48 | 2.80 | 2.94 |
|  | Aspect ratio | 1.8 | 3.5 | 2.6 | 3.0 |
| Physical properties of coating film | Total light transmittance 1 (%) | 15 | 13 |  |  |
|  | Total light transmittance 2 (%) | 16 | 10 |  |  |
|  | Total light transmittance 3 (%) | 54 | 11 |  |  |
|  | Parallel light transmittance 1 (%) | 85 | 55 |  |  |
|  | Parallel light transmittance 2 (%) | 93 | 83 |  |  |

From the results of examples described above, it is evident that the hexagonal prism-shaped zinc oxide particles of the present invention are excellent in transparency and have excellent ultraviolet blocking performance. Further, it is evident that the hexagonal prism-shaped zinc oxide particles have excellent ultraviolet blocking performance in a wavelength range of UVA at 375 nm. On the other hand, the zinc oxide particles of Comparative Examples 1 to 3 were unsatisfactory in transparency or ultraviolet blocking performance, and therefore could not have both of these physical properties. Especially for the zinc oxide particles of Comparative Example 3 having a primary particle diameter of 0.02 μm, sufficient ultraviolet blocking performance could not be achieved in a wavelength range of UVA at 375 nm. When a reaction was carried out under the conditions of Comparative Example 4, hexagonal plate-shaped zinc oxide particles were formed, and the hexagonal prism-shaped zinc oxide particles of the present invention could not be obtained. When a reaction was carried out under the conditions of Comparative Example 5, indefinite-shaped zinc oxide particles having a primary particle diameter of 0.65 μm, which included hexagonal plate-shaped particles, were formed, and the hexagonal prism-shaped zinc oxide particles of the present invention having a primary particle diameter of less than 0.5 μm could not be obtained. When a reaction was carried out under the conditions of Comparative Example 6, rod-shaped zinc oxide particles having a large aspect ratio were formed, and the hexagonal prism-shaped zinc oxide particles of the present invention having an aspect ratio of less than 2.5 could not be obtained.

INDUSTRIAL APPLICABILITY

The hexagonal prism-shaped zinc oxide particles of the present invention can be used as a component of a cosmetic, a heat releasing filler, a heat releasing resin composition, a heat releasing grease and a heat releasing coating composition.

The invention claimed is:

1. Hexagonal prism-shaped particles consisting of zinc oxide having a primary particle diameter of 0.1 μm or more and less than 0.5 μm and an aspect ratio of less than 2.5.

2. The hexagonal prism-shaped particles according to claim 1, which are obtained by aging zinc oxide fine particles as a seed in an aqueous solution in which a zinc salt is dissolved.

3. The hexagonal prism-shaped particles according to claim 1 wherein the D90/D10 in particle size distribution is 2.4 or less.

4. A method for production of the particles according to claim 1, comprising a step of aging zinc oxide fine particles as a seed in an aqueous solution in which a zinc salt is dissolved.

5. A cosmetic comprising the hexagonal prism-shaped particles according to claim 1.

6. A heat releasing filler comprising the hexagonal prism-shaped particles according to claim 1.

7. A heat releasing resin composition comprising the hexagonal prism-shaped particles according to claim 1.

8. A heat releasing grease comprising the hexagonal prism-shaped particles according to claim 1.

9. A heat releasing coating composition comprising the hexagonal prism-shaped particles according to claim 1.

10. The hexagonal prism-shaped particles according to claim 2, wherein the D90/D10 in particle size distribution is 2.4 or less.

11. A method for production of the particles according to claim 2, comprising a step of aging zinc oxide fine particles as a seed in an aqueous solution in which a zinc salt is dissolved.

12. A method for production of the particles according to claim 3, comprising a step of aging zinc oxide fine particles as a seed in an aqueous solution in which a zinc salt is dissolved.

13. A cosmetic comprising the hexagonal prism-shaped particles according to claim 2.

14. A cosmetic comprising the hexagonal prism-shaped particles according to claim 3.

15. A heat releasing filler comprising the hexagonal prism-shaped particles according to claim 2.

16. A heat releasing filler comprising the hexagonal prism-shaped particles according to claim 3.

17. A heat releasing resin composition comprising the hexagonal prism-shaped particles according to claim 2.

18. A heat releasing resin composition comprising the hexagonal prism-shaped particles according to claim 3.

19. A heat releasing grease comprising the hexagonal prism-shaped particles according to claim 2.

20. A heat releasing grease comprising the hexagonal prism-shaped particles according to claim 3.

21. Hexagonal prism-shaped particles consisting of zinc oxide having a primary particle diameter of 0.1 μm or more and less than 0.5 μm and an aspect ratio of less than 2.5, wherein the hexagonal prism-shaped particles are surface-treated.

22. A cosmetic comprising the hexagonal prism-shaped particles according to claim 21.

23. A heat releasing filler comprising the hexagonal prism-shaped particles according to claim 21.

24. A heat releasing resin composition comprising the hexagonal prism-shaped particles according to claim 21.

25. A heat releasing grease comprising the hexagonal prism-shaped particles according to claim 21.

26. A heat releasing coating composition comprising the hexagonal prism-shaped particles according to claim 21.

* * * * *